(12) United States Patent
Colato et al.

(10) Patent No.: US 7,739,859 B2
(45) Date of Patent: Jun. 22, 2010

(54) APPARATUSES AND METHODS FOR STERILISING AND FILLING COMPONENTS OF PACKAGING UNITS PARTICULARLY BOTTLES AND/OR CAPS

(75) Inventors: Luca Colato, Montechiarugolo (IT); Angelo Silvestri, Ricco del Golfo di Spezia (IT)

(73) Assignee: Sidel S.p.A., Parma (IT)

( * ) Notice: Subject to any disclaimer, the term of this patent is extended or adjusted under 35 U.S.C. 154(b) by 0 days.

(21) Appl. No.: 11/579,684

(22) PCT Filed: May 5, 2005

(86) PCT No.: PCT/IB2005/001222

§ 371 (c)(1),
(2), (4) Date: Nov. 7, 2006

(87) PCT Pub. No.: WO2005/108278

PCT Pub. Date: Nov. 17, 2005

(65) Prior Publication Data

US 2007/0237672 A1  Oct. 11, 2007

(30) Foreign Application Priority Data

May 7, 2004  (IT) .......................... MO2004A0111

(51) Int. Cl.
B65B 55/08  (2006.01)
(52) U.S. Cl. ............................. 53/426; 53/471; 53/167; 53/282
(58) Field of Classification Search .................. 53/167, 53/426, 471, 282; 422/22; B65B 55/08
See application file for complete search history.

(56) References Cited

U.S. PATENT DOCUMENTS

| 2,561,404 | A | * | 7/1951 | Nordquist | .................... 53/167 |
| 3,780,308 | A | | 12/1973 | Nablo | |
| 4,652,763 | A | * | 3/1987 | Nablo | .................... 250/492.3 |
| 4,944,132 | A | | 7/1990 | Carlsson et al. | |
| 5,088,231 | A | * | 2/1992 | Kertz | .................... 47/1.01 R |
| 5,848,515 | A | * | 12/1998 | Catelli et al. | .................. 53/167 |
| 6,230,472 | B1 | * | 5/2001 | Stahlecker | .................... 53/426 |

(Continued)

FOREIGN PATENT DOCUMENTS

CA  2289464 A1 * 5/1998

(Continued)

OTHER PUBLICATIONS

Machine translation of JP 2000-281183, from Japanese Patent Office, http://www4.ipdl.inpit.go.jp/Tokujitu/tjsogodbenk.ipdl, 7 pages, retrieved Mar. 16, 2009.*

(Continued)

Primary Examiner—Stephen F Gerrity
(74) Attorney, Agent, or Firm—Nixon & Vanderhye P.C.

(57) ABSTRACT

An apparatus comprises a rotating conveying system for conveying along a curved path components of packaging units comprising containers and container closures, a filling device for filling with a product the containers on the rotating conveying system, a sterilizing device for sterilizing at least part of the components mounted along the path and comprising an irradiating device arranged to emit radiation.

17 Claims, 8 Drawing Sheets

U.S. PATENT DOCUMENTS 7,299,606 B2 * 11/2007 Bonatti et al. .............. 53/473
2004/0222224 A1 * 11/2004 Plester .............. 220/203.17

FOREIGN PATENT DOCUMENTS

| DE | 39 27 491 A1 | | 2/1991 |
| --- | --- | --- | --- |
| DE | 40 39 434 A1 | | 6/1992 |
| DE | 195 20 925 A1 | | 12/1996 |
| DE | 199 09 826 A1 | | 9/2000 |
| DE | 19909826 A1 | * | 9/2000 |
| JP | 05042995 A | * | 2/1993 |
| JP | 2000281183 A | * | 10/2000 |
| JP | 2002068144 A | * | 3/2002 |
| JP | 2004067233 A | * | 3/2004 |
| WO | WO 9304930 A1 | * | 3/1993 |
| WO | 98/42385 | | 10/1998 |
| WO | WO 98/51609 A1 | * | 11/1998 |

OTHER PUBLICATIONS

International Search Report of PCT/IB2005/001222, mailed Dec. 20, 2005.

* cited by examiner

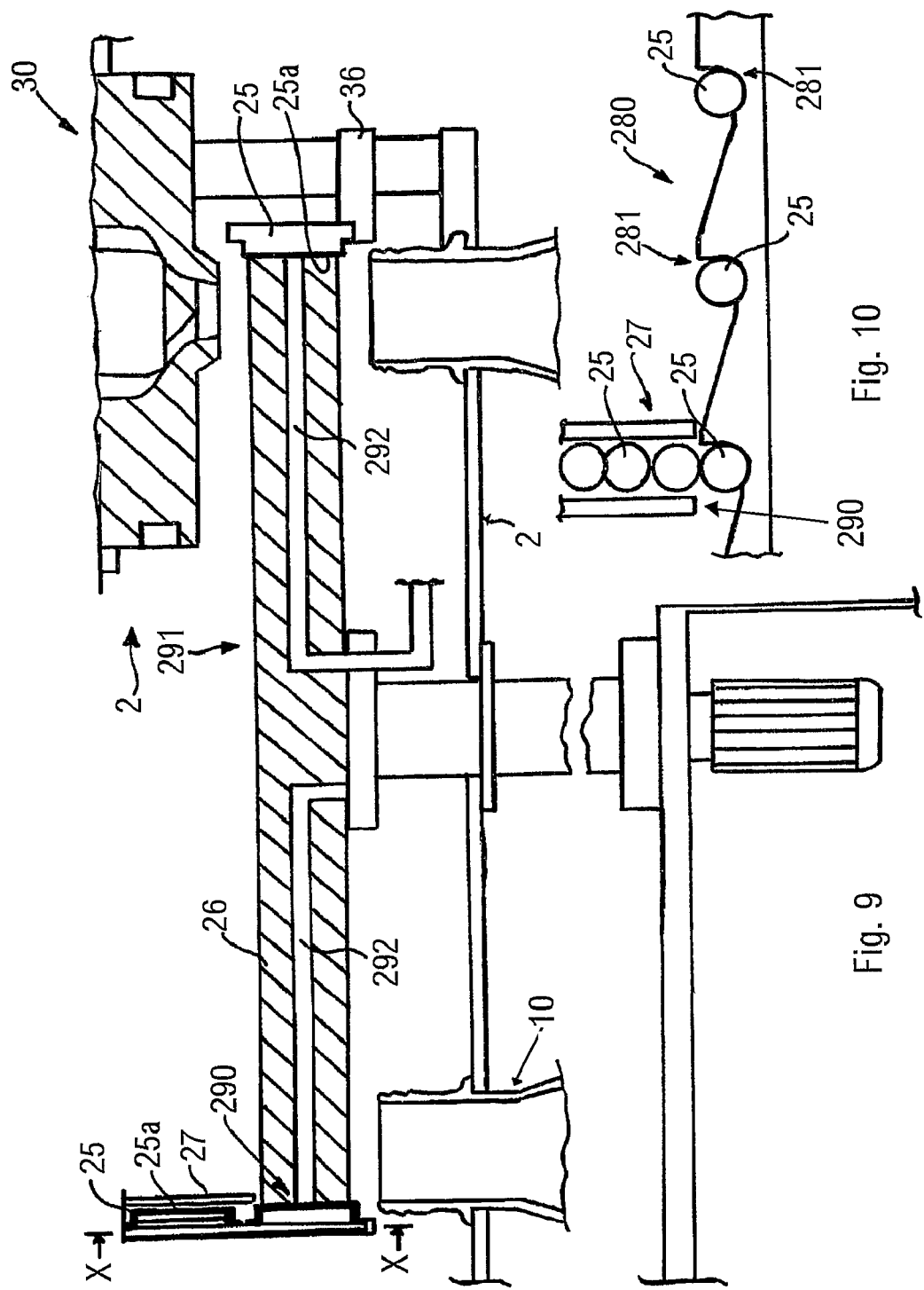

APPARATUSES AND METHODS FOR STERILISING AND FILLING COMPONENTS OF PACKAGING UNITS PARTICULARLY BOTTLES AND/OR CAPS

This application is the US national phase of international application PCT/IB2005/001222, filed 5 May 2005, which designated the U.S. and claims priority of IT MO2004A000111, filed 7 May 2004, the entire contents of each of which are hereby incorporated by reference.

The invention relates to apparatuses and methods for filling and sterilising components of packaging units, in particular bottles and/or caps. Such apparatuses and methods are particularly suitable for being used to obtain bottles filled and/or sealed in aseptic conditions.

In the production of filled containers, in particular of containers intended to be filled with foodstuffs such as milk or fruit juice or other drinks, it is very important to ensure that both the containers and their contents and the caps are sterile and safe for the health of the consumer. To this end, it is necessary to sterilise both internally and externally the containers before filling them, to sterilise the caps with which to close the containers, fill and close or seal the containers in an aseptic environment to avoid their contamination after sterilisation.

Different techniques are known from the prior art for sterilising containers to be filled.

The containers can be treated with a chemical sterilising agent with great oxidising power, such as for example derived chloride, hydrogen peroxide or peracetic acid, or mixtures of the latter. This procedure comprises different phases: the containers are first wet internally and externally with the sterilising agent that is left in contact with the walls of the container for a sufficient time so that the sterilisation reaction occurs, this sterilisation reaction being dependent on the concentration, the action time and the temperature of the sterilising agent; subsequently, the containers are rinsed with sterile water to eliminate residues of the sterilising agent used, or, in the case of hydrogen peroxide, are fanned with heated air to evaporate the residues.

A limit arising from the use of a chemical agent for sterilising containers is that such a technique requires rather a long time for all the phases that the procedure requires to be completed.

This causes delays in the manufacturing process of filled containers.

A further limit is connected to the very great overall dimensions required by an apparatus to manufacture filled containers in aseptic conditions that uses a chemical sterilising agent. It is in fact necessary to provide a wetting station, a rinsing station or drying station, a filling station and a cap-fitting station. Furthermore, all the stations listed above must be maintained in an environment that has been made sterile by means of isolators, or be placed inside a so-called "clean room".

To maintain the aseptic conditions in an isolator, or in a "clean room" it is necessary to filter the air with suitable filters before inserting it inside the protected environments; furthermore, in order to avoid undesired infiltrations of air, such environments are kept at pressure that is greater than atmospheric pressure.

The plant and running costs for an apparatus that is provided with large aseptic environments are therefore very high.

A further limit is that chemical sterilisation cannot be used with all containers. In particular, chemical sterilising agents leave residues in PET (polyethylene terephthalate) bottles, so there are limits to their use.

A still further limit is that in chemical sterilisation processes high temperatures are often reached that can alter the chemical-physical properties of the containers and cause alterations to the material of which they are made that are for example due to crystallisation.

This is evident above all for bottles in PET as this material is very sensitive to high temperatures.

From WO2004/000100 it is furthermore known sterilising empty containers already provided with caps with a beam of electrons in a suitable irradiation chamber, filling said containers inside the irradiation chamber by perforating the wall of the cap with a filling needle, conveying the filled containers outside the irradiation chamber and applying thermal energy to the cap to close the hole caused by the filling needle and again sealing the container.

A limit to this method is that the thermal treatment to which the filled containers are subjected may alter the product inside the containers. This is particularly important in cases in which foodstuffs are present in the containers, as there is a risk that after thermal treatment such foodstuffs will become unusable or hazardous for the health of a consumer.

A further limit is that such a method cannot be used with all types of cap but only with caps that are easily perforable by a filling nozzle.

It is furthermore known, for example from U.S. Pat. No. 3,780,308, using electron beams to sterilise empty containers previously placed in an aseptic sterilisation zone, filling the containers, closing the containers with a portion of previously sterilised sealing tape and conveying the closed and filled containers outside the aseptic zone.

The known solutions are suitable for treating containers with a widened shape, such as trays or the like, but are not suitable for treating containers with an elongated shape, such as bottles, which have an inlet section that is reduced in relation to the body.

In fact, in the treatment of bottles there arises the problem of penetration of radiation and the efficacy of sterilisation treatment of all the internal surface of the bottles.

Furthermore, the known solutions enable sealed containers to be produced i.e. containers which cannot be reclosed once they have been opened but those solutions are nevertheless not suitable for producing containers provided with caps that enable subsequent opening and closing of the containers.

Furthermore, known apparatuses have a considerable spatial extent to arrange in succession the different treatment stations, therefore the aseptic conditions must be maintained in a very extensive zone, with the consequent problems of high costs for managing such plants.

An object of the invention is to improve the apparatuses and the methods for obtaining components of sterile packaging units or bottles filled and capped in sterile conditions.

A further object is to produce an apparatus for obtaining sterile, filled containers, or caps, having limited spatial dimensions and high productivity.

A still further object is to produce apparatuses and methods per obtaining sterile filled containers that can be used with containers made of any material and be provided with a cap of any desired type.

A still further object is to provide an apparatus and a method for sterilising containers that ensures great efficacy of treatment even for containers having great axial extent and great capacity.

In a first aspect of the invention, there is provided an apparatus comprising a rotating conveying system for conveying along a curved path components of packaging units comprising containers and container closures, a filling device for filling with a product said containers on said rotating conveying system, a sterilising device for sterilising at least part of said components, characterised in that said sterilising device is mounted along said path.

Owing to this aspect of the invention, it is possible, at the same level of productivity, to greatly reduce the overall spatial dimensions of a system for obtaining filled sterile containers. It is furthermore possible to greatly reduce the spatial extent of the aseptic zone of such apparatuses.

In a second aspect of the invention, there is provided an apparatus a comprising rotating conveying system for conveying along a curved path components of packaging units comprising containers and container closures, a filling device for filling with a product said containers on said rotating conveying system, a sterilising device for sterilising at least part of said components, characterised in that said sterilising device comprises an irradiating device arranged to emit radiation.

In a third aspect of the invention, there is provided a method comprising conveying along a curved path components of packaging units comprising containers and container closures, filling with a product said containers during said conveying, sterilising at least part of said components, characterized in that said sterilising comprises irradiating said containing components with radiation.

Owing to these aspects of the invention, it is possible to obtain filled sterile containers made from any desired product and in which the efficacy of sterilisation is very high.

It is furthermore possible to obtain effective sterilisation of the containers without having to proceed to wetting and to subsequent drying of the walls of the containers that have to be sterilised.

In a fourth aspect of the invention, there is provided an apparatus comprising a rotating carousel arrangement to convey containers, a filling device for filling said containers on said rotating carousel arrangement, characterised in that said rotating carousel arrangement comprises an applicator member of container closures arranged to apply said container closures to said containers.

This enables the dimensions of a sterile environment in which the containers are filled to be further reduced.

In a fifth aspect of the invention, there is provided a method for obtaining filled containers comprising conveying containers by a carousel arrangement, filling said containers on said rotating carousel arrangement, sterilising said containers upstream of said carousel arrangement, characterised in that said method furthermore comprises applying container closures to said containers on said rotating carousel arrangement.

A capping apparatus may also be provided that is positioned downstream of said carousel arrangement and is arranged to apply a closing cap to each container.

In a sixth aspect of the invention there is provided an apparatus comprising a conveying system of components of packaging units for conveying said components to a sterile zone, an irradiation device of radiation to irradiate said components, characterised in that an orientation device is provided such that said irradiation device is directed at each surface zone to be sterilised of said components.

The orientation device can act on the components of the packaging units and/or of the irradiation device.

The orientation device may comprise a rotation member arranged to rotate, below said irradiation device, said components around a longitudinal axis of said components.

In a seventh aspect of the invention, a method is provided comprising conveying components of packaging units to a sterile zone, irradiating said components with a suitable irradiation device, characterised in that during said irradiating reciprocally moving said components in relation to said irradiation device is provided for, such as to irradiate each surface zone to be sterilised of said components.

Owing to these aspects of the invention, it is possible to sterilise in an effective manner the entire external but above all internal surface of the containers, preventing that, because of shading due to particular container shapes, zones inside the container are not reached by irradiation and are therefore not sterile.

In this way it is furthermore possible to sterilise by irradiation in a very effective manner containers having an elongated shape, such as bottles even with great capacity.

In an eighth aspect of the invention there in provided an apparatus comprising a conveying system of container closures, an applicator member of said container closures on containers, characterised in that along said conveying system of container closures an irradiation device is arranged to irradiate said closures of containers with sterilising radiation.

In a ninth aspect of the invention a method is provided comprising conveying container closures, applying said container closures to containers, characterised in that during said conveying irradiating said closures of containers with sterilising radiation is provided for.

The invention will be better understood and carried out with reference to the attached drawings that show an embodiment thereof by way of non-limitative example, in which:

FIG. 9 is a section like the one in FIG. 8, but in another embodiment;

FIG. 10 is a fragmentary section taken along a plane X-X in FIG. 9.

Figure 1:
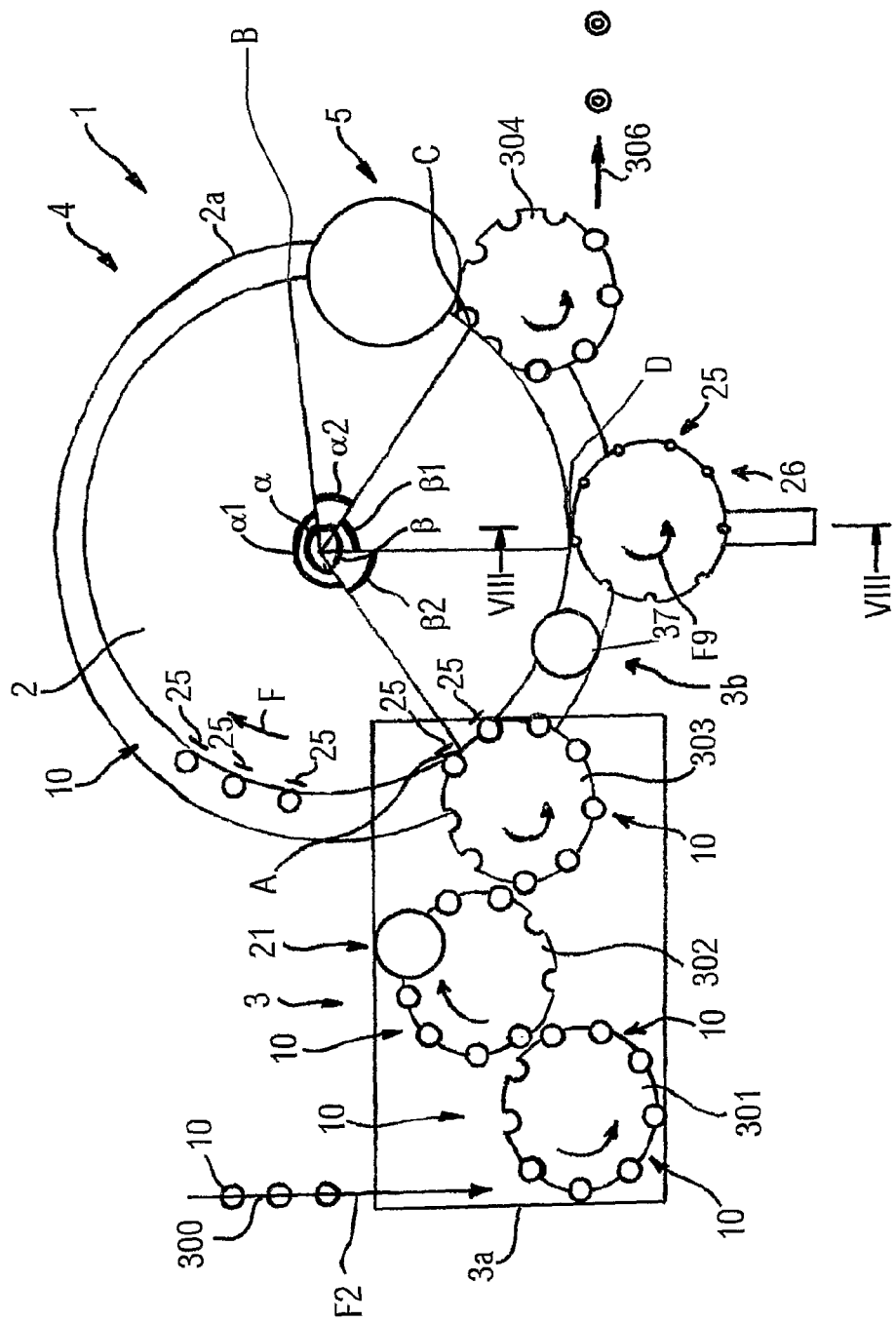
FIG. 1 is a simplified schematic plan view of an embodiment of an apparatus for the production of filled sterile containers.

With reference to FIG. 1, an apparatus 1 is shown for producing filled sterile containers.

The apparatus 1 comprises a carousel 2 delimited by walls 2a having the function of insulating the carousel 2 from the outside to ensure that aseptic conditions are maintained inside it. Upstream of the carousel 2, a sterilisation zone 3 is provided, which is also aseptic, is delimited by walls 3a, in which empty containers 10 are sterilised, in particular bottles coming from a supply line 300. In the sterilisation zone 3 there are arranged a first conveying star 301, a second conveying star 302 and a third conveying star 303 that are rotatable around their respective vertical and interacting axes such as to shift the containers 10 from the supply line 300 to an inlet A of the carousel 2 along a snaking path that goes through an irradiation sterilising device 21.

The carousel 2 rotates in the direction indicated by the arrow F, conveying in its rotation the containers 10 and/or container closures 25 that have to be treated in suitable treatment zones provided on the carousel 2 and arranged in succession.

The treatment zones are defined as follows.

The containers 10 that enter the carousel 2 from the inlet A are rotated by the carousel to an outlet C at which the containers 10 are removed from the carousel 2 and go to a further conveying star 304 by means of which they are evacuated along an evacuation line 306.

Between the inlet A and the outlet C an active sterilisation zone α is defined comprising a filling sector α1, corresponding to a filling zone 4, in which the containers 10 that are on board the carousel 2 are filled with a product and a sealing sector α2, having a lesser extent than α1, in which the filled containers 10, that continue to be conveyed on the carousel 2, are sealed by the container closures 25 in a sealing zone 5.

Between the outlet C and the inlet A a passive angular sector β is defined along which the carousel 2 is devoid of the containers 10.

The passive sector β comprises a loading sector β1, comprised between the outlet C and a further inlet D along which the carousel 2 interacts with a loading star 26 to remove from it the container closures 25 and drag them in its rotation in the direction indicated by the arrow F.

The passive sector β furthermore comprises a sterilisation sector β2, corresponding to the zone also known as the "dead angle" of the carousel 2, comprised between the further inlet D and the inlet A, corresponding to a further sterilisation zone 3b, along which the container closures 25 loaded on the carousel 2 are sterilised by a further irradiation sterilising device 37.

The carousel 2 then conveys along the active zone a both the containers 10 and the container closures 25, one container closure for each container 10.

The evacuation line 306 takes the containers 10, each one of which is equipped with a container closure 25, to a capping machine that is not shown in which the containers 10 provided with the closures 25 are definitively capped with suitable caps, for example screw caps.

In this embodiment, the capping machine does not need to be located in an aseptic environment, because the containers 10 that abandon the outlet A cannot be contaminated in the parts in contact with the product because each container is equipped with a container closure 25 that prevents undesired contamination.

This enables the construction and management costs of a capping machine to be used with this apparatus embodiment to be drastically reduced.

This embodiment of the apparatus 1 thus enables overall dimensions to be further reduced.

With the apparatus shown in FIG. 1 sterile filled containers 10 are obtained that are provided with a cap in two parts, a sealing container closure 25 and a cap proper that is placed on the container closure 25.

Figure 2:
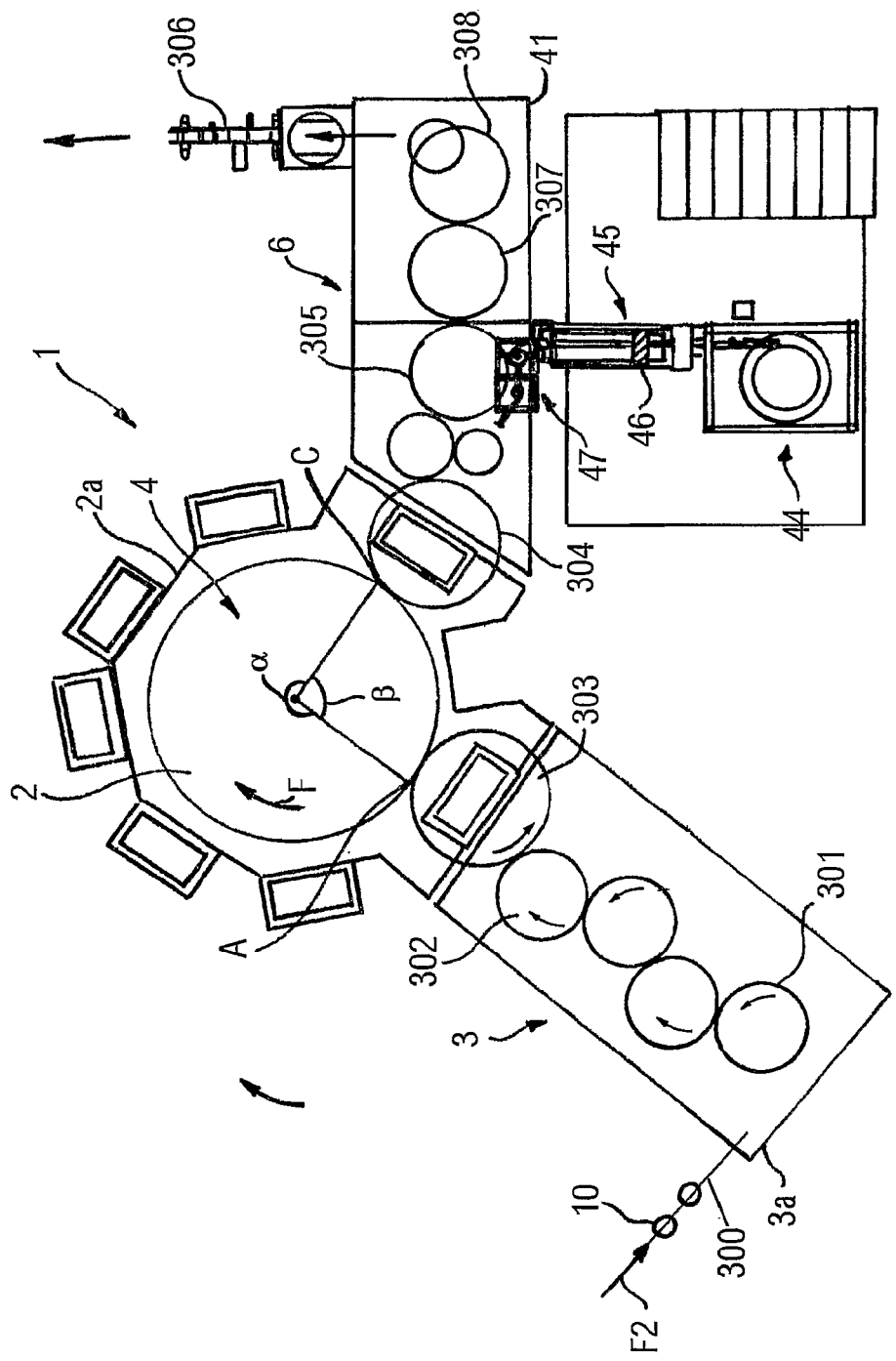
FIG. 2 is a simplified schematic plan view of a further embodiment of an apparatus for the production of filled sterile containers.

With reference to FIG. 2, an apparatus 1 is shown that enables filled containers 10 to be obtained that have a single-piece cap.

The apparatus 1 corresponds to what has been disclosed with reference to FIG. 1, but is devoid of the loading star 26. Consequently, in the wheel 2 only the containers 10 are conveyed to the active sector α, whilst the carousel 2 is devoid of container closures in the active sector α.

The filled containers 10 that leave the carousel 2 at the outlet C are transported by the further conveying star 304 that transfers the containers 10 to a second further conveying star 305 that takes the containers to a third further conveying star 307 from which the containers 10 go to a fourth further conveying star 308 that takes them to the evacuation line 306.

The further conveying stars 304, 305, 307, 308 take the filled containers 10 along a snaking outlet path that passes through a capping machine 6 in which the filled containers 10 are capped with suitable previously sterilised caps that are picked up from a storage zone 44 and reach a capping device 47 through a conveying tunnel 45 on which an irradiation sterilising device 46 is positioned.

The capping machine 6 is arranged inside an aseptic environment delimited by walls 41 that ensure conditions of sterility of the filled containers 10 and of the relative caps.

The sterile capping machine 6 is connected to a storage zone of the caps 44 from which the caps are removed and conveyed through a conveying tunnel 45.

Figure 3:
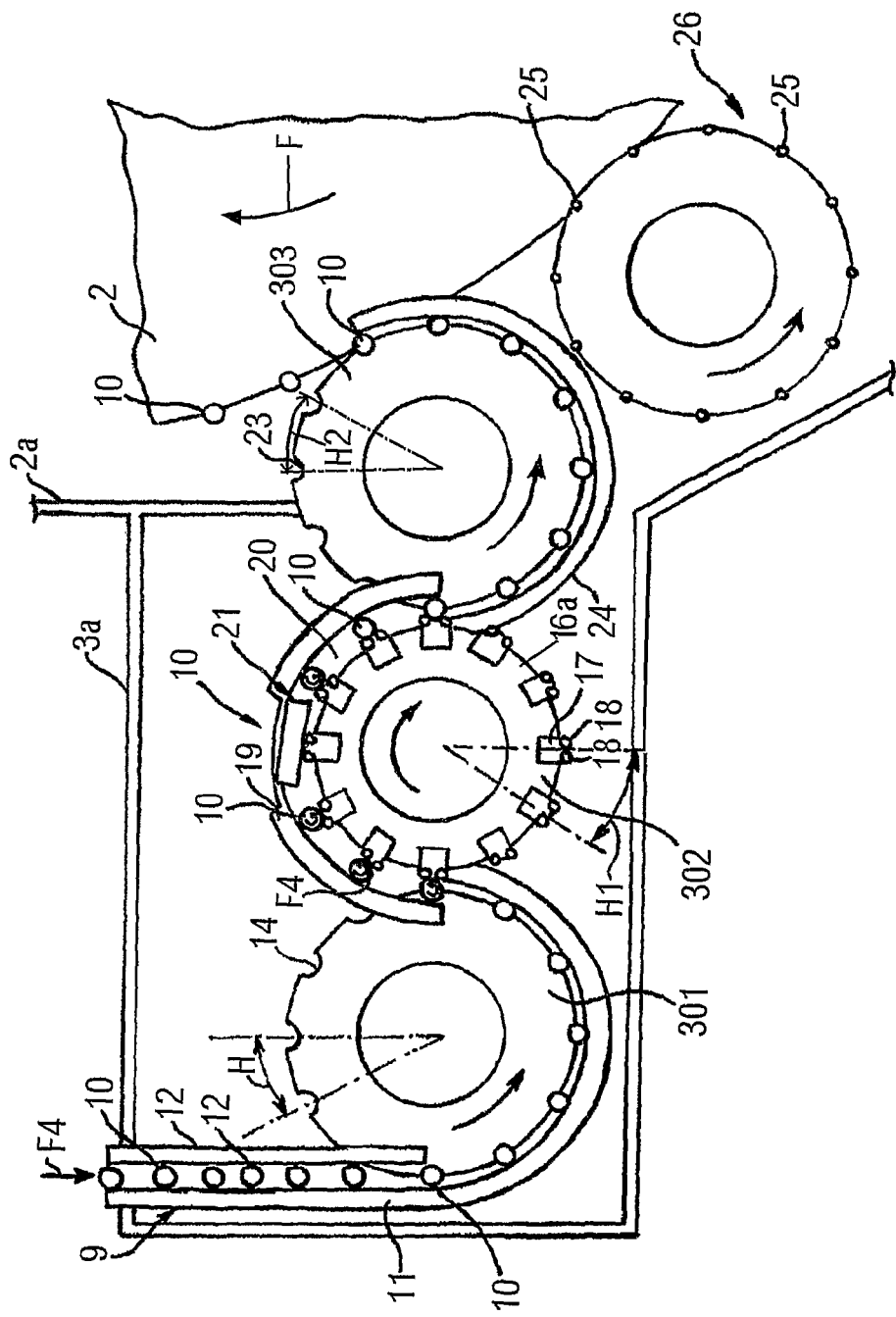
FIG. 3 is a schematic view from above of an embodiment of the sterilisation zone of an apparatus for producing filled sterile containers, as shown in FIGS. 1, or 2.

With reference to FIG. 3, the sterilisation zone 3 is shown in greater detail that is part of the apparatus in FIG. 1 and/or 2.

The two embodiments of the sterilisation zone 3 presented in FIGS. 1 and 2 differ by number of conveying stars provided for conducting the containers 10 from the supply line of the containers 300 to the carousel 2; that number can be suitably varied according to particular needs.

Into the sterilisation zone 3 suitably filtered sterile air is delivered from suitable filters that are not shown and is kept at a certain overpressure to avoid undesired infiltration from the exterior.

The containers 10 are supplied to the sterilisation zone 3 by moving them in the direction F2 along the supply line 300, by means of an overhead conveyor 9 provided with first a guide device 11 and with second guide device 12 between which the containers 10 remain engaged during conveying.

Figure 5:
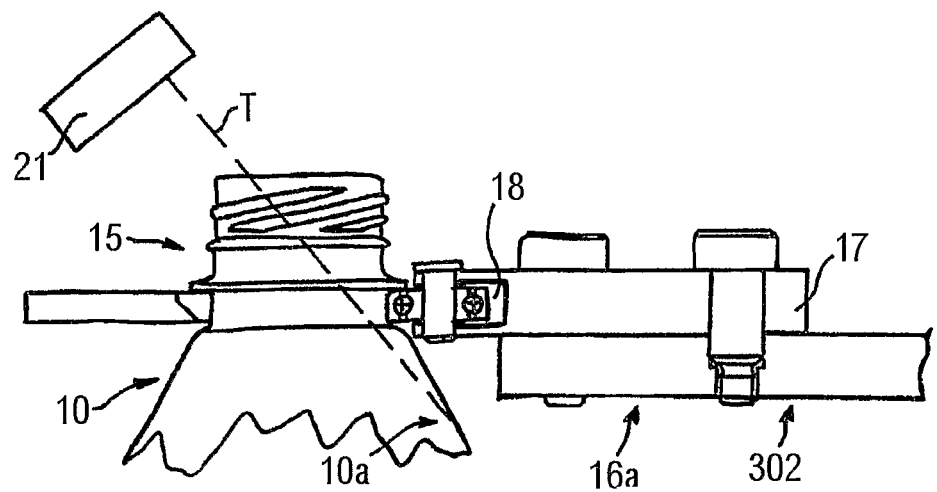
FIG. 5 is a schematic section taken along a plane V-V in FIG. 4.

The overhead conveyor 9 takes the containers 10 to the first conveying star 301 peripherally provided with seats 14 spaced by an angular pitch H and shaped in such a way that portions of neck 15 of the containers 10 engage inside them, as shown in FIG. 5.

The first guide device 11 of the overhead conveyor 9 is formed in such a way as to guide the containers 10 during their rotation on the first conveying star 301 to prevent the container to exit from the seats 14 during this rotation movement.

The containers 10, after a set path on the first conveying star 301, are picked up by a second conveying star 302 rotating on the same rotation plane as the first conveying star 301, but in opposite direction.

On a peripheral sterilisation zone 16a of the second conveying star 302 a plurality of supports 17 is fixed, on each of which a pair of idle rolling bodies 18 is mounted and located at an angular pitch H1, the angular pitch H1 may also be the same as H.

Outside the second conveying star 302 a guide 19 is provided arranged to guide the containers 10 and located at a distance from each pair of rolling bodies 18 so that between the latter and the guide 19 a seat 20 is identified inside which the containers 10 are received.

Figure 4:
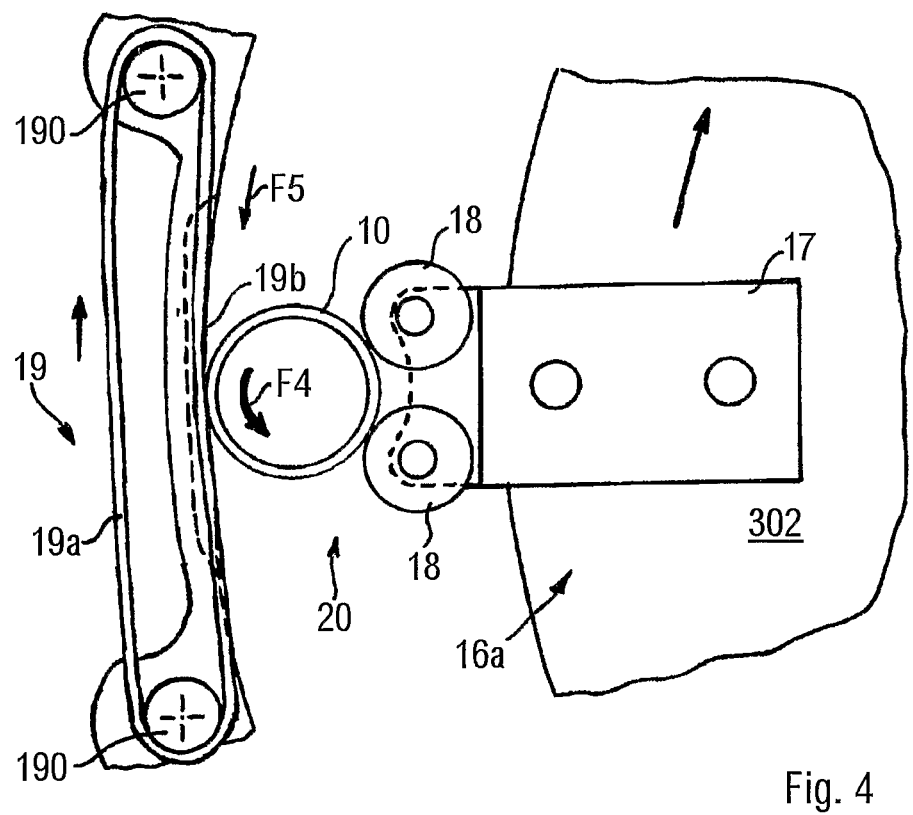
FIG. 4 is an enlarged detail of FIG. 3.

As shown in FIG. 4, the guide 19 is provided with a closed loop track 19a on a pair of pulleys 190 and moved by a drive apparatus that is not shown such that a surface 19b of the track 19a placed in contact with a container 10 to be conveyed translates in the translation direction F5 and causes in the container 10 to be conveyed a rotation in a direction indicated by the arrow F4 opposite the rotation direction of the second conveying star 302.

Thus the containers 10, when they are on the second conveying star 302, are subject to an internal revolution around the axis of the second conveying star 302 and to a rotation movement around their own longitudinal axis indicated by F4.

The second conveying star 302 conveys the containers 10 to the operating zone of an irradiation sterilising device, such as an electron gun 21, which irradiates the containers 10 with beta rays, i.e. with electron rays having high energy.

Each container 10 performs at least one complete rotation around its axis in a time corresponding to the time in which the second conveying star 302 covers a distance that is the same as angular pass H1. In this way, a container 10 that is in the operating zone of the electron gun 21 performs underneath it a complete rotation before a further container 10 adjacent to the operating zone of the electron gun 21 arrives in said operating zone.

The electron gun 21 is supplied by a VDC electron accelerator that provides power amounting to 350-400 keV and enables about 600-800 bottles a minute to be treated, ensuring their sterilisation provided that any desired internal and/or external surface zone of the containers 10 receives a radiation dose between 10 and 20 kGy.

The electron gun 21 is positioned in such a way that the beam of electrons emitted in relation to each container 10 has a trajectory indicated by T in FIG. 5, that has an angle of incidence on an internal wall 10a of the containers 10 such as to ensure a reflection of the beam that ensures penetration of the beam and therefore effective sterilisation over the whole height of the containers 10.

By rotating the containers 10 below the electron gun 21, it is furthermore possible to irradiate points of the internal surface 10a of the containers 10 located on the entire internal surface thereof, thus sterilising the entire internal surface 10a of the containers 10.

The position of the electron gun 21 in relation to the containers 10 and its operating features enable the neck zone 15 and the thread of the containers 10 to be treated precisely and effectively.

In this way, it is possible to effectively treat even containers having an elongated shape and a whatever complex shape and with a capacity between 0.2 liters and about 2 liters.

Further positioning devices can also be provided in relation to the rolling bodies 18 which, during irradiation, move the electron gun 21 in relation to the containers 10, or vice versa, or move both the electron gun 21 and the containers 10, such as to position the beam of electrons emitted by the electron gun 21 effectively on all the points of the internal surface 10a of the containers 10.

In a further embodiment, a gas injection device is provided that is arranged to inject noble gas inside the containers 10 during their irradiation by the electron gun 21.

In this way, inside the containers 10 gas plasma with great sterilising power is created, the sterilisation capacity of which cooperates with that of the beam of electrons, increasing the efficacy of sterilisation treatment.

The containers 10 are subsequently moved by the second conveying star 302 to a third conveying star 303, rotating in the same rotation direction as the first conveying star 301 and formed in a similar manner to the first conveying star 301, i.e. peripherally provided with further seats 23 placed at an angular pitch H2, inside which the neck portions 15 of the containers 10 engage.

The third conveying star 303 cooperates with a further guide 24 to convey the containers 10 to the carousel 2.

The values of the angular pitches H, H1, H2, and the values of the speed rotation of the first conveying star 301, of the second conveying star 302 and of the third conveying star 303 are selected such as to enable a synchronised shift of the containers 10 inside the sterilisation zone 3 and the carousel 2.

Figure 6:
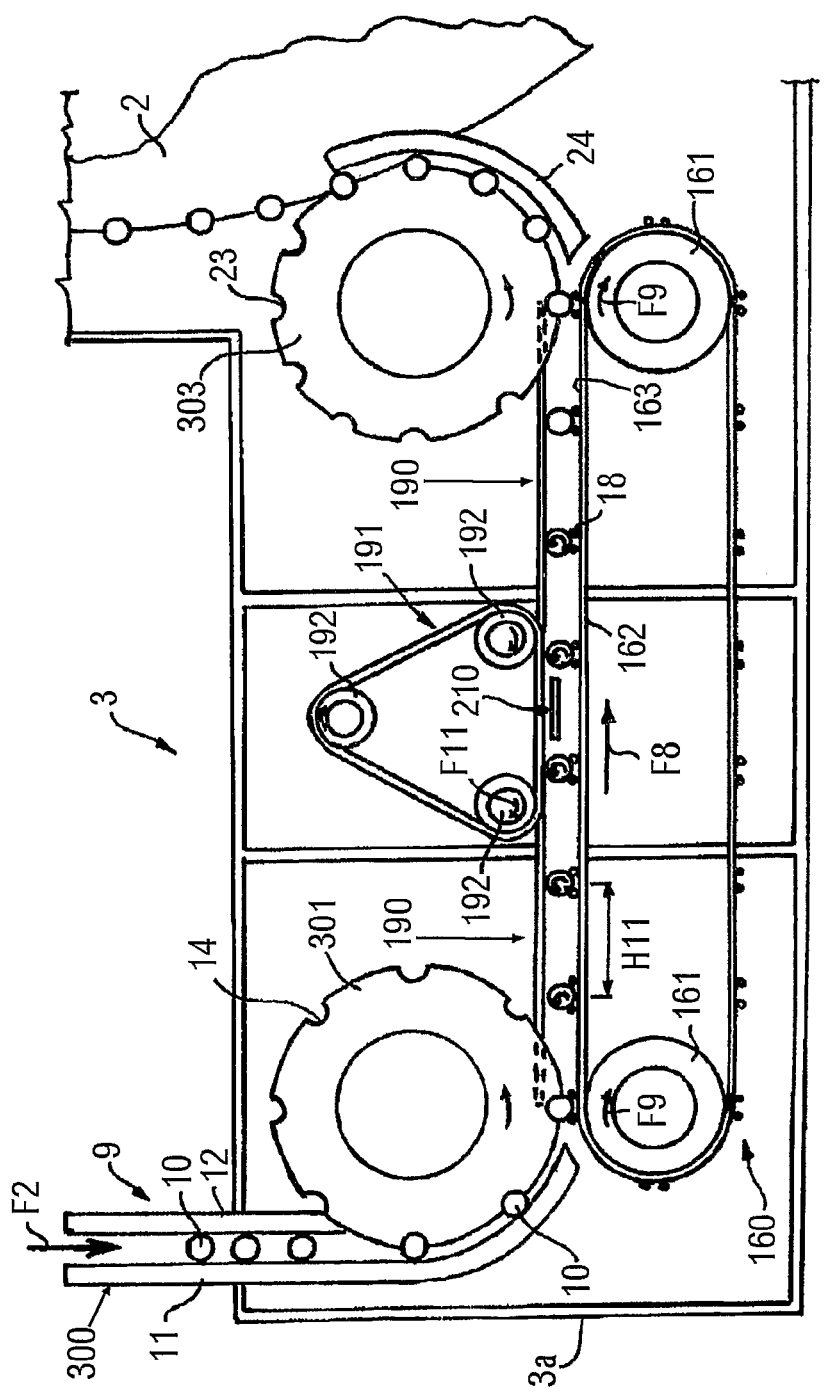
FIG. 6 is a schematic view like the one in FIG. 3 but of another embodiment.
Figure 7:
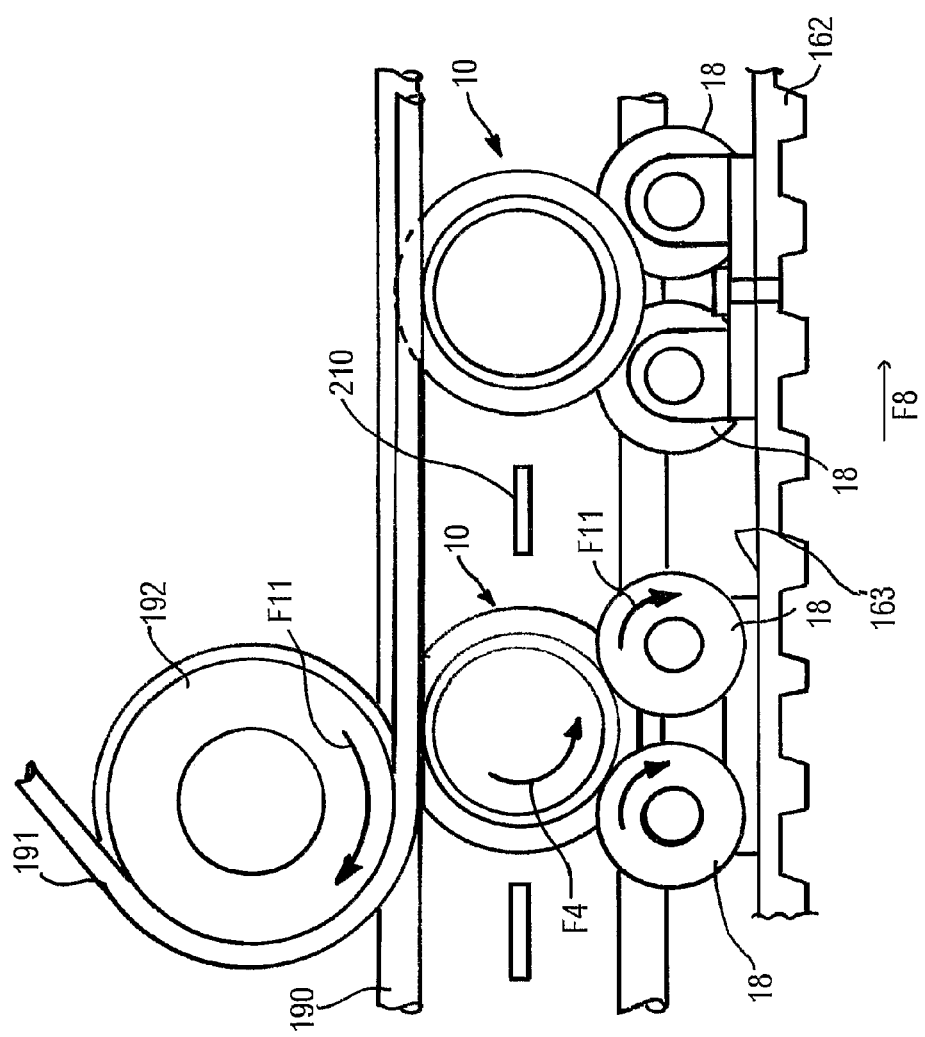
FIG. 7 is an enlarged and fragmentary detail of FIG. 6.

With reference to FIG. 6, an embodiment of the sterilisation zone 3 is shown in which instead of the second conveying star 302 there is provided a linear conveyor 160 such as a belt conveyor.

The belt conveyor 160, which is moved by a pair of driven guide wheels 161 between which a belt 162 is wound, conveys the containers 10 in a translation direction F8 to the third conveying star 303.

On an external surface 163 of the belt 162 a plurality of pairs of rolling bodies 18 is provided.

Outside the belt 162, a straight guide 190 is provided that is arranged in such a way as to accompany the containers 10 during their translating motion onto the belt 162.

The guide 190, in its interrupted portion, is replaced by a further track 191 wound as a loop on further guide wheels 192 arranged according to the vertices of a triangle having a side corresponding to the guide 190, the guide wheels rotating in the direction F11 through the effect of the drive apparatus that is not shown.

The further track 191 is positioned such as to interact with an external surface of the containers 10 to rotate them in direction F4, onto the rolling bodies 18 while they translate in direction F8.

At the same time, the rolling bodies 18 are rotated in the direction F11.

The containers 10 are conveyed from the belt conveyor 160 to the operating zone of an electron gun 21 that irradiates the containers 10 with beta rays, i.e. with a beam of electrons having high energy.

Also in this case, the position of the electron gun 21 in relation to the containers 10, i.e. the angle of incidence of the beam of electrons emitted by it is such as to ensure rapid and effective sterilisation of the internal and external surface of the containers 10.

Each container 10 performs at least one complete rotation, rotates around its own longitudinal axis below the electron gun 21.

A gas-injection device can also be provided that is arranged to inject noble gas inside the containers 10 during their irradiation with the electron gun 21.

In this way plasma gas with high sterilising power is generated inside the containers 10, the sterilising capacity of which cooperates with that of the beam of electrons to increase the efficacy of the sterilisation treatment.

Figure 8:
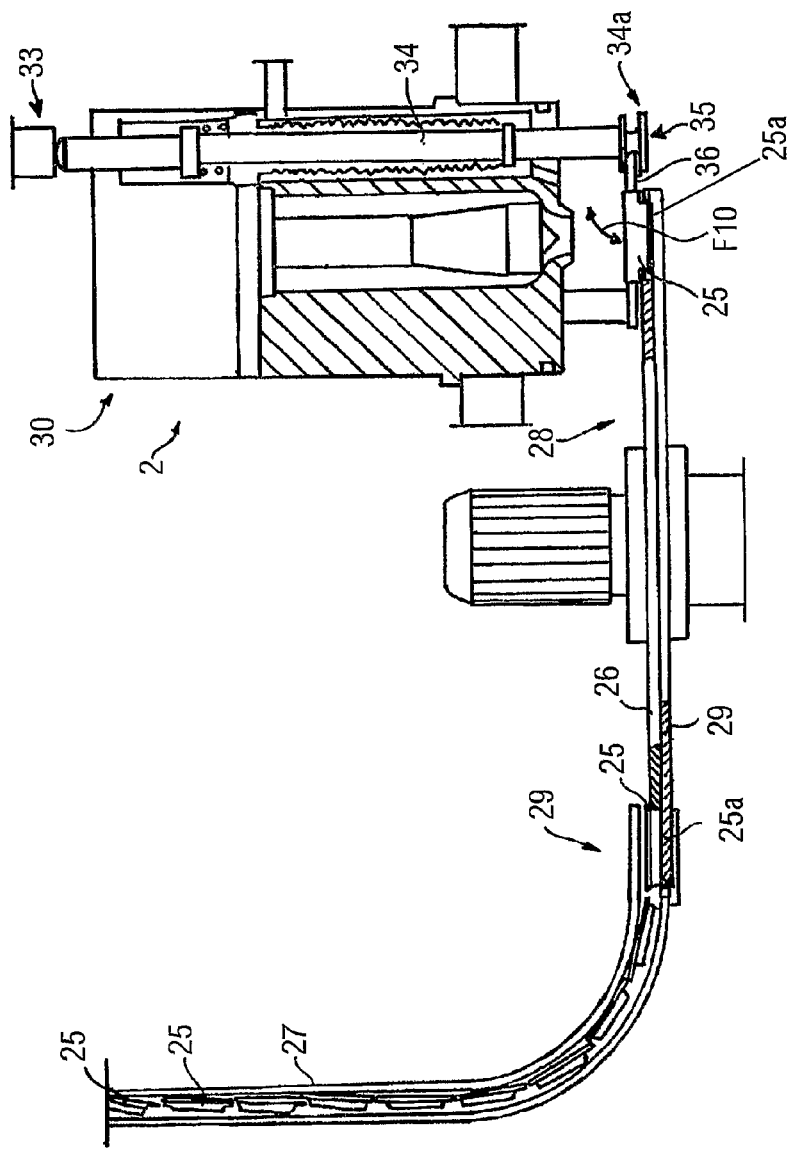
FIG. 8 is a schematic and fragmentary section taken along a plane VIII-VIII in FIG. 1.

With reference to FIG. 8, a loading star 26 is shown that is arranged to supply container closures 25 to the carousel 2 at the further inlet D.

The container closures 25 coming from a hopper, which is not shown, are conveyed in sequence through a conveying conduit 27 to an outlet 29 in which the container closures 25 are in a horizontal position and face the loading star 26 rotating in the direction indicated by F9, opposite the rotation direction F of the carousel 2.

Each container closure 25 is pushed against the periphery of the loading star 26 such as to be received in one of the peripheral seats with which the latter is provided. In this way the container closures 25 are taken to the edge of the loading star and are transferred to the carousel 2 to the operating zone of a given filling device 30 of containers of the plurality of filling devices with which the carousel 2 is provided.

The filling device 30 can be any known filling device and has therefore not been disclosed.

In the proximity of the filling device 30 there is provided a cam 33 that causes a bar element 34 to shift along its own longitudinal axis.

At one end 34a of the bar element 34 located at the part opposite the cam 33 there is provided a seat element 35 shaped such as to receive an oscillating arm 36 that is arranged to remove the container closures 25 from the peripheral seats of the loading star 26 and take them to the edge of the carousel 2.

By actuating the cam 33 the bar element 34 is translated, i.e. it is lowered or raised to rotate the oscillating arm 36 connected with it as indicated by the arrow F10.

In order to remove the container closures 25 from the loading star 26, the arm 36, which is first in a vertical position, is rotated such as to engage from above with a container closure 25 and is subsequently rotated in the opposite direction to return to the initial position after picking up a container closure 25.

The carousel 2 transfers the container closures 25 to the further sterilisation zone 3b, where they are irradiated by a further irradiating device, such as a further electron gun 37 arranged, as shown in FIG. 1, on the periphery of the carousel 2.

The further electron gun 37 irradiates the container closures 25 with a beam of electrons such as to ensure complete and effective sterilisation.

In the conveying position, the container closures 25 are arranged on the filling device 30 in such a way that their surface 25a, arranged to be in contact with the inside of the containers 10, faces the further electron gun 37.

For the further electron gun 37 and its operation the same considerations apply as those made for the electron gun 21 and for sterilisation of the containers 10.

Sterilisation of the container closures 25 is therefore very fast and occurs in the time required to cover the space between the further inlet D and the inlet A, or between the inlet of the containers 10 on the carousel 2.

In this way it is possible to sterilise container closures 25 on a carousel 2.

After sterilisation, each container closure 25 continues to rotate on the carousel 2 anchored to the respective oscillating arm 36.

The carousel 2, during its rotation, carries each filling device 30, provided with a sterilised container closure 25, to the inlet A of the containers 10, where the sterile containers 10 are removed from the carousel 2, each container being positioned at a filling device 30 and being rotatingly conveyed.

From the inlet A, as each container 10 is positioned at a filling device 30, filling of the containers 10 with a desired flowing product occurs.

Filling of the containers 10 occurs over a time corresponding to rotation of the carousel 2 along the filling sector α1 and can be considered to be terminated at the filling point B.

Subsequently, the filled containers 10 are conveyed to the sealing zone 5, that is still arranged on the carousel 2, in which each oscillating arm 36 is again rotated into a horizontal position and by interference applies the respective container closure 25 to each container 10.

With reference to FIGS. 9 and 10, there is shown an alternative embodiment of a device for loading and sterilising container closures 25 on the carousel 2, in which the container closures 25 are conveyed through the conduit 27 to an outlet 290 in which the container closures 27 are in a vertical position.

The outlet 290 faces the periphery of the loading star 26, provided with a serrated-edge 280 surface.

On the surface 280 of the loading star 26 there is identified a plurality of seats 281, each arranged to receive a given container closure 25.

The loading star 26 is internally provided with a plurality of hollow passages 292 each of which terminates in a seat 281 and can be alternatively connected to a suction device arranged to create a desired vacuum, or to a compression device arranged to supply pressurised air to the inside of the channel 292.

The container closures 25 fall from the conveying conduit 27 to the seats 281 inside which they are arranged so that their surface 25a, that in use is directed inside a container 10, is in contact with the periphery of the loading star 26.

When a container closure 25 falls into a seat 280 a certain vacuum is created inside the channel 292, in such a way as to keep the container closure 25 in the desired position.

When, during rotation of the loading star 26, a position near the carousel 2 is reached, the container closures 25 are each removed through interference by an oscillating arm 36 that is located in a vertical position and are each conveyed to a filling device 30 on the carousel 2.

Subsequently, the container closures 25 are conveyed to the further electron gun 37, which irradiates them with sterilising radiation.

In the sealing zone 5, when the container closures 25 have to be applied to the filled containers 10, the oscillating arm 36 causes the container closures 25 to rotate by about 90° to take them to a horizontal position so as to apply them by interference to the containers 10.

After the container closures 25 have been applied to each filled container 10, the filled and sealed containers 10 can be conveyed outside the aseptic carousel 2, and any subsequent operations to which the containers have to be subjected can be performed in non-aseptic environments.

The invention claimed is:

1. Apparatus, comprising a rotating conveying system for conveying along a curved path components of packaging units comprising containers and container closures, a filling device for filling with a product said containers on said rotating conveying system, a sterilising device for sterilising at least part of said components, said sterilising device being mounted along said path, said sterilising device comprising a first sterilising device for sterilising said containers arranged upstream of a carousel of said rotating conveying system in which said containers are filled and provided with said container closures, wherein said sterilising device further comprises a second sterilising device for sterilising said container closures on said carousel, said second sterilising device being arranged on the periphery of said carousel, wherein said sterilising device comprises an irradiating device arranged to emit a beam of electrons, and further comprising an orientation device for positioning said beam of electrons, said orientation device being arranged to direct said beam of electrons to sterilise each surface zone of said container closures;

and wherein said sterilising device comprises a further irradiating device arranged to emit a further beam of electrons and a further orientation device for positioning said further beam of electrons, said further orientation device being arranged to direct said further beam of electrons to each surface zone to sterilise said containers;

said further beam of electrons having a trajectory inclined with respect to the vertical axis of the container such that an angle of incidence on an internal wall of the container ensures a reflection of the further beam that ensures penetration of said further beam over the whole height of the container;

said beam of electrons having a trajectory inclined with respect to the vertical axis of the container closure such that an angle of incidence on an internal wall of the container closure ensures a reflection of the beam that ensures penetration of the beam over the whole height of the container closure; and said orientation device being provided for relative movement between said beam of electrons and said container closure, said further orientation device being provided for relative movement between said further beam of electrons and said containers.

2. Apparatus according to claim 1, wherein said first sterilising device is mounted on a conveying wheel apparatus of said rotating conveying system.

3. Apparatus according to claim 1, wherein said first sterilising device is mounted on a linear conveying apparatus interposed between said rotating conveying system.

4. Apparatus according to claim 1, wherein said second sterilising device is mounted in a zone of a blind angle of said carousel.

5. Apparatus according to claim 4, wherein said carousel has a zone for the application of said container closures located downstream of a filling zone of said carousel.

6. Apparatus according to claim 1, wherein said carousel has a zone for the application of said container closures located downstream of a filling zone of said carousel.

7. Apparatus according to claim 1, wherein said sterilising device comprises a gas inserting system suitable for producing plasma when it is irradiated by said further beam of electrons.

8. Method, comprising conveying along a curved path components of packaging units comprising containers and container closures, filling with a product said containers on a rotating conveying system, sterilising at least part of said components using a sterilising device mounted along said path, said sterilising device comprising first and second sterilising devices, said method further comprising sterilising with said first sterilising device containers arranged upstream of a carousel in which said containers are filled and provided with said container closures, said sterilising further comprising sterilising said container closures on said carousel with said second sterilising device arranged on the periphery of said carousel, and providing an irradiating device arranged to emit a beam of electrons and an orientation device for positioning said beam of electrons, and directing said beam of electrons to sterilise each surface zone of said container closures, said sterilising further comprising:
providing a further irradiating device arranged to emit a further beam of electrons and a further orientation device for positioning said further beam of electrons, said further orientation device being arranged to direct said further beam of electrons to each surface zone to sterilise said containers;

inclining a trajectory of said further beam of electrons with respect to the vertical axis of the container such that an angle of incidence on an internal wall of the container ensures a reflection of the further beam that ensures penetration of said further beam over the whole height of the container;

inclining a trajectory of said beam of electrons with respect to the vertical axis of the container closure such that an angle of incidence on an internal wall of the container closure ensures a reflection of the beam that ensures penetration of the beam over the whole height of the container closure; and providing said orientation device for relative movement between said beam of electrons and said container closure, and providing said further orientation device for relative movement between said further beam of electrons and said containers.

9. Method according to claim 8, wherein said sterilising comprises emitting a further beam of electrons to said components.

10. Method according to claim 9, wherein said sterilising occurs in such a way as to produce plasma from gaseous substances in said components.

11. Method according to claim 8, wherein said sterilising occurs in such a way as to produce plasma from gaseous substances in said components.

12. Apparatus, comprising a rotating conveying system for conveying along a curved path components of packaging units comprising containers and container closures, a filling device for filling with a product said containers on said rotating conveying system, a sterilising device for sterilising at least part of said components, said sterilising device being mounted along said path, said sterilising device comprising a first sterilising device for sterilising said containers arranged upstream of a carousel of said rotating conveying system in which said containers are filled and provided with said container closures, wherein said sterilising device further comprises a second sterilising device for sterilising said container closures on said carousel, said second sterilising device being arranged on the periphery of said carousel, wherein said sterilising device comprises an irradiating device arranged to emit a beam of electrons, and further comprising an orientation device for positioning said beam of electrons, said orientation device being arranged to direct said beam of electrons to each surface zone to sterilise said container closures;

and wherein said sterilising device comprises a further irradiating device arranged to emit a further beam of electrons, said further beam of electrons having a trajectory inclined with respect to the vertical axis of the container such that an angle of incidence on an internal wall of the container ensures a reflection of the further beam that ensures penetration of said further beam over the whole height of the container.

13. Apparatus, comprising a rotating conveying system for conveying along a curved path components of packaging units comprising containers and container closures, a filling device for filling with a product said containers on said rotating conveying system, a sterilising device for sterilising at least part of said components, said sterilising device being mounted along said path, said sterilising device comprising a first sterilising device for sterilising said containers arranged upstream of a carousel of said rotating conveying system in which said containers are filled and provided with said container closures, wherein said sterilising device further comprises a second sterilising device for sterilising said container closures on said carousel, said second sterilising device being arranged on the periphery of said carousel, wherein said sterilising device comprises an irradiating device arranged to emit a beam of electrons, and further comprising an orientation device for positioning said beam of electrons, said orientation device being arranged to direct said beam of electrons to each surface zone to sterilise said container closures;

and wherein said orientation device being provided for relative movement between said beam of electrons and said container closure.

14. Apparatus, comprising a rotating conveying system for conveying along a curved path components of packaging units comprising containers and container closures, a filling device for filling with a product said containers on said rotating conveying system, a sterilising device for sterilising at least part of said components, said sterilising device being mounted along said path, said sterilising device comprising a first sterilising device for sterilising said containers arranged upstream of a carousel of said rotating conveying system in which said containers are filled and provided with said container closures, wherein said sterilising device further comprises a second sterilising device for sterilising said container closures on said carousel, said second sterilising device being arranged on the periphery of said carousel, wherein said sterilising device comprises an irradiating device arranged to emit a beam of electrons, and further comprising an orientation device for positioning said beam of electrons, said orientation device being arranged to direct said beam of electrons to each surface zone to sterilise said container closures;

and wherein said sterilising device comprises a further irradiating device arranged to emit a further beam of electrons and a further orientation device for positioning said further beam of electrons, said further orientation device being arranged to direct said further beam of electrons to each surface zone to sterilise said containers;

said beam of electrons and/or said further beam of electrons having a trajectory inclined with respect to the vertical axis of the container closure and/or the container such that an angle of incidence on an internal wall of the container closure and/or the container ensures a reflection of the beam and/or the further beam that ensures penetration of the beam and/or the further beam over the whole height of the container closure and/or the container; and said orientation device being provided for relative movement between said beam of electrons and said container closure, said further orientation device being provided for relative movement between said further beam of electrons and said containers.

15. Method, comprising conveying along a curved path components of packaging units comprising containers and container closures, filling with a product said containers on a rotating conveying system, sterilising at least part of said components using a sterilising device mounted along said path, said sterilising device comprising first and second sterilising devices, said method further comprising sterilising with said first sterilising device containers arranged upstream of a carousel in which said containers are filled and provided with said container closures, said sterilising further comprising sterilising said container closures on said carousel with said second sterilising device arranged on the periphery of said carousel, and providing an irradiating device arranged to emit a beam of electrons and an orientation device for positioning said beam of electrons, and directing said beam of electrons to each surface zone to sterilise said container closures, said sterilising further comprising:
providing a further irradiating device arranged to emit a further beam of electrons; and
inclining a trajectory of said further beam of electrons with respect to the vertical axis of the container such that an angle of incidence on an internal wall of the container ensures a reflection of the further beam that ensures penetration of said further beam over the whole height of the container.

16. Method, comprising conveying along a curved path components of packaging units comprising containers and container closures, filling with a product said containers on a rotating conveying system, sterilising at least part of said components using a sterilising device mounted along said path, said sterilising device comprising first and second sterilising devices, said method further comprising sterilising with said first sterilising device containers arranged upstream of a carousel in which said containers are filled and provided with said container closures, said sterilising further comprising sterilising said container closures on said carousel with said second sterilising device arranged on the periphery of said carousel, and providing an irradiating device arranged to emit a beam of electrons and an orientation device for positioning said beam of electrons, and directing said beam of electrons to each surface zone to sterilise said container closures, said sterilising further comprising providing said orientation device for relative movement between said beam of electrons and said container closure.

17. Method, comprising conveying along a curved path components of packaging units comprising containers and container closures, filling with a product said containers on a rotating conveying system, sterilising at least part of said components using a sterilising device mounted along said path, said sterilising device comprising first and second sterilising devices, said method further comprising sterilising with said first sterilising device containers arranged upstream of a carousel in which said containers are filled and provided with said container closures, said sterilising further comprising sterilising said container closures on said carousel with said second sterilising device arranged on the periphery of said carousel, and providing an irradiating device arranged to emit a beam of electrons and an orientation device for positioning said beam of electrons, and directing said beam of electrons to each surface zone to sterilise said container closures, said sterilising further comprising:
providing a further irradiating device arranged to emit a further beam of electrons and a further orientation device for positioning said further beam of electrons, said further orientation device being arranged to direct said further beam of electrons to each surface zone to sterilise said containers;
inclining a trajectory of said beam of electrons and/or said further beam of electrons with respect to the vertical axis of the container closure and/or the container such that an angle of incidence on an internal wall of the container closure and/or the container ensures a reflection of the beam and/or the further beam that ensures penetration of the beam and/or the further beam over the whole height of the container closure and/or the container; and
providing said orientation device for relative movement between said beam of electrons and said container closure, and providing said further orientation device for relative movement between said further beam of electrons and said containers.

* * * * *